United States Patent [19]

Foster

[11] Patent Number: 4,480,108

[45] Date of Patent: Oct. 30, 1984

[54] PROCESS FOR SEPARATION OF TOCOPHEROL HOMOLOGUES

[75] Inventor: Charles H. Foster, Kingsport, Tenn.

[73] Assignee: Eastman Kodak Company, Rochester, N.Y.

[21] Appl. No.: 519,477

[22] Filed: Aug. 1, 1983

[51] Int. Cl.³ ............................................. C07D 311/72
[52] U.S. Cl. ..................................... 549/413; 548/540
[58] Field of Search ................................ 549/413, 411

[56] References Cited

U.S. PATENT DOCUMENTS 3,402,182  9/1968  Kijima et al. ..................... 549/413
4,191,692  3/1980  Grafen et al. ..................... 549/411

Primary Examiner—Nicky Chan
Attorney, Agent, or Firm—Clyde L. Tootle; Daniel B. Reece, III

[57] ABSTRACT

A process for separating the various members of a tocopherol homologue mixture to obtain fractions of the separate tocopherol homologues. The isolation of the various tocopherol homologues is accomplished by selective deacylation of tocopheryl esters followed by separation of the esters from the free tocopherols.

6 Claims, No Drawings

PROCESS FOR SEPARATION OF TOCOPHEROL HOMOLOGUES

DESCRIPTION

This invention relates to a process for separating the various tocopherol homologues from mixtures of the tocopherol homologues. The isolation of the various tocopherol homologues is accomplished by selective deacylation of tocopheryl esters followed by separation of the esters from the free tocopherols.

Heretofore, various processes have been used for separating and isolating the various tocopherol homologues, for example, the α-tocopherol vitamin E. The gamma and delta tocopherol homologues are useful as antioxidants. One previous method for separating and isolating the various homologues has been accomplished by ion exchange chromatography, as noted in U.S. Pat. No. 3,402,182, or liquid chromatography. However, because of the very small difference in structure of the various tocopherol homologues, these separation processes require large quantities of adsorbent or resins. Also, these processes are useful mainly only for isolating δ-tocopherol from mixtures of α- and δ-tocopherol. Therefore, it would be an advance in the state of the art to provide a more efficient process for separation of the various tocopherol homologues from mixtures of such homologues.

In accordance with the present invention, it has been discovered that cyclic amines deacylate tocopheryl esters in the order $\delta > \beta \sim \gamma >> \alpha$. Moreover, α-tocopheryl esters are relatively inert. Therefore, by choosing the appropriate reaction time and temperature, a mixture of tocopheryl ester homologues treated with non-aromatic saturated cyclic amines having 5 to 6 ring members will provide a mixture of δ-tocopherol and β-, γ-, and α-tocopheryl esters or δ-, β-, and γ-tocopherols with α-tocopheryl ester. The simple separation of the ester fraction from the tocopherol fraction by any of several methods (e.g., chromatography, ion exchange, distillation) leads to a separation of tocopherols.

Generally, reacting the mixed tocopheryl acetates (α, β, γ, and δ) with cyclic amines, such as pyrrolidine, which, for example, in a suitable solvent at room temperature leads to rapid deacylation of δ-tocopheryl acetate (~15 minutes). The acetates of β- and γ-tocopherol react more slowly (~2 hours) and α-tocopheryl acetate does not react. These rate differences are sufficient to allow selective deacetylation of β-, γ-, and δ-acetates in the presence of α-acetate. Since the polarity of the acetate is significantly different from that of the free tocopherol, this allows an efficient chromatographic isolation of α-tocopheryl acetate. In addition, if one begins with a mixture that is mainly γ- and α-tocopheryl acetates (such as is obtained after removal of δ-tocopherol from natural tocopherol concentrates with basic ion-exchange resins), selective deacylation of γ-acetate 3 allows simple chromatographic purification of γ-tocopherol, 3b.

Scheme I

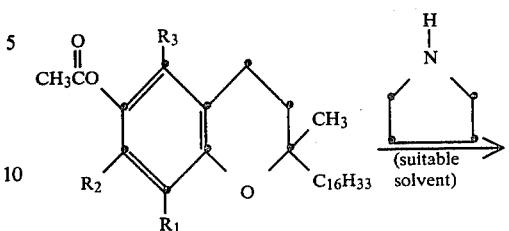

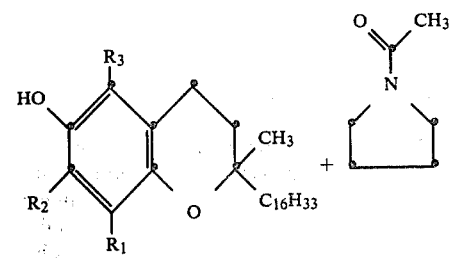

α = 1: $R_1 = R_2 = R_3 = CH_3$ 1b
β = 2: $R_1 = R_3 = CH_3$; $R_2 = H$ 2b
γ = 3: $R_1 = R_2 = CH_3$; $R_3 = H$ 3b
δ = 4: $R_1 = CH_3$; $R_2 = R_3 = H$ 4b

The chromatographic separation can even be made easier by the use of longer chain esters than those shown in Scheme I. For example, the selective deacylation is effective for the hexanoates of tocopherols, although at a slower rate than for the tocopheryl acetates. This process was used to prepare 96% pure γ-tocopherol. First the δ-tocopherol was removed by selective deacylation of δ-tocopheryl hexanoate followed by chromatographic separation of the δ-tocopherol from the remaining tocopheryl hexanoates. Then the γ-tocopherol was isolated by selective deacylation of γ-tocopheryl hexanoate followed by chromatographic separation of the γ-tocopherol from the α-tocopheryl hexanoate (see Scheme II). (It should also be possible to effect separation of esters from free tocopherols by molecular distillation if longer chain esters are used.)

Scheme II

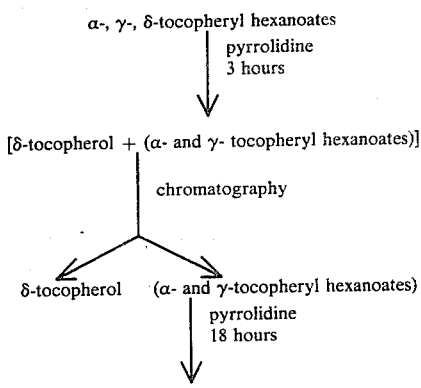

-continued
Scheme II

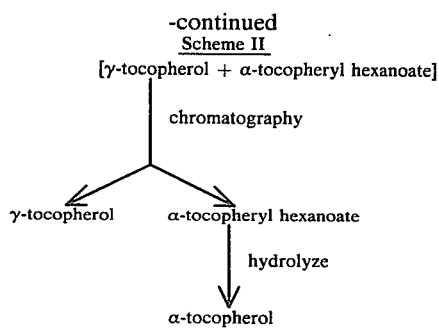

[γ-tocopherol + α-tocopheryl hexanoate] → chromatography → γ-tocopherol / α-tocopheryl hexanoate → hydrolyze → α-tocopherol Cyclic amines useful in the present invention are, for example, piperidine, morpholine, pyrrolidine, and the like. Especially useful are the cyclic five member ring amines such as pyrrolidine.

Pyrrolidine is uniquely suited for rapid reaction under mild conditions. Deacetylation with morpholine can be accomplished in neat morpholine at room temperature at longer reaction times. A suitable solvent can be used. A suitable solvent is one which dissolves the two compounds. Such suitable solvents include dichloromethane, toluene, benzene, and the like.

The reaction rate is dependent on the reaction temperature, the particular amine used, and the amount of the particular cyclic amine being used. For example, reacting pyrrolidine at ambient temperature with a 10 to 1 molar ratio of cyclic amine to tocopherol acetate deacylates the δ-tocopheryl acetate in from 5 to 30 minutes and the β- and γ-tocopheryl acetates in from about 1½ hours to about 4 hours. Repeating the process at temperatures higher than ambient temperatures increases all of the reaction rates. Also, increasing the ratio of cyclic amine to tocopheryl acetate also increases the deacylation reaction rates. Likewise, lowering the reaction temperatures below ambient temperature and lowering the ratio of cyclic amine to tocopheryl acetate to less than about 10 to 1 lowers the deacylation reaction rates. Also, pyrrolidine reacts much faster than morpholine while acyclic amines such as diethylamine are unreactive.

This invention can be further illustrated by the following examples of preferred embodiments thereof, although it will be understood that these examples are included merely for purposes of illustration and are not intended to limit the scope of the invention unless otherwise specifically indicated.

EXAMPLE 1

Fifty grams of a mixed tocopherol concentrate derived from soybean oil deodorizer distillates (5.5%, α; 0.7%, β; 25.9%, γ; 11.7%, δ; 43.8% total tocopherols) was dissolved in 250 mL of dry pyridine and hexanoyl chloride (28.8 g, 30 mL) was added slowly at 15° C. The mixture was stirred at room temperature for three hours and then poured into H$_2$O. Extraction with ether followed by washing with aqueous HCl, water and brine, and then drying over MgSO$_4$ and evaporation gave the acylated product (71 g). A 5-g portion of this product was dissolved in 15 mL of CH$_2$Cl$_2$ and 5 mL of pyrrolidine. After the solution was stirred for three hours at room temperature, all the δ-hexanoate had deacylated but essentially none of the γ-hexanoate and only 30% of the γ-hexanoate had reacted. The mixture was acidified with aqueous HCl and extracted with CH$_2$Cl$_2$; and the CH$_2$Cl$_2$ extract was washed with dilute HCl, dried over MgSO$_4$, and concentrated to 4.79 g of oil. Silica gel chromatography was conducted by first eluting the esters with 2% acetone in heptane and then eluting the free tocopherols with 5% acetone in heptane. The tocopherol hexanoate fraction (now only γ- and α-hexanoates) was then further treated for about 18 hours with pyrrolidine/CH$_2$Cl$_2$ to deacylate γ-tocopherol hexanoate and then chromatographed on silica gel as above to give γ-tocopherol (96% pure) and α-tocopheryl hexanoate. The α-tocopheryl hexanoate can be converted to a α-tocopherol by simple saponification.

EXAMPLE 2

To 20.4 g of a mixture of tocopheryl acetates (37%, α; 1.4%, β; 29.9%, γ; 25.5%, δ) dissolved in 120 mL CH$_2$Cl$_2$ under N$_2$ was added 10 g of pyrrolidine. After stirring for eighteen hours at room temperature, the mixture was analyzed by glpc and showed complete deacylation of the δ- and γ-acetates. The mixture was acidified with aqueous HCl, washed with H$_2$O, dried over MgSO$_4$, and concentrated to 21.3 g of an oil. Chromatography on Doucil adsorbent (3% acetone/hexane) gave 5.8 g of α-tocopheryl acetate, cleanly separated from β-, γ-, and δ-tocopherols.

EXAMPLE 3

A solution of 1.5 g of α-tocopheryl acetate and 1.5 g of δ-tocopheryl acetate in 25 ml of morpholine was stirred at room temperature for 8 hours. Morpholine was distilled off at room temperature under vacuum. The resulting oil was dissolved in ether and washed with 10% aqueous HCl followed by H$_2$O. The ether solution was dried over MgSO$_4$ and evaporated to give 2.9 g of oil which was shown by glpc analysis to be δ-tocopherol and α-tocopheryl acetate. The ester and free-tocopherol fractions can be separated as in the examples above.

The invention has been described in detail with particular reference to preferred embodiments thereof, but it will be understood that variations and modifications can be effected within the spirit and scope of the invention.

I claim:

1. A process for separating the tocopherol homologues which comprises reacting the acylated tocopherol mixture with at least one non-aromatic saturated cyclic amine to deacylate one group of tocopheryl esters thereby enabling separation of the tocopherol homologue mixture into an alpha tocopherol homologue fraction, a fraction containing the beta-gamma tocopherol homologues and a delta tocopherol homologue fraction.

2. A process for isolating α-tocopheryl esters from other tocopheryl ester homologues (β-, γ-, and δ-tocopheryl esters) according to claim 1 which comprises reacting the mixture of esters with at least one non-aromatic saturated cyclic amine to deacylate the β-, γ-, and δ-tocopheryl esters, then separating the α-tocopheryl ester fraction from the tocopherol fraction.

3. A process for isolating beta-gamma tocopherol homologues from a mixture of tocopherol ester homologues according to claim 1 which comprises: (1) reacting the mixture of esters with at least one cyclic amine to deacylate predominantly the δ-tocopheryl esters, (2) isolation of the remaining tocopheryl esters, (3) reacting the remaining isolated tocopheryl esters with non-aromatic saturated cyclic amine to provide a mixture of free beta-gamma tocopherols and α-tocopheryl ester, and (4) separation of the tocopherol components from the α-tocopheryl ester.

4. A process for separating the tocopherol homologues which comprises reacting the acylated tocopherol mixture with pyrrolidine to deacylate one group of tocopheryl esters thereby enabling separation of the tocopherol mixture into an alpha tocopherol homologue fraction, a fraction containing the beta-gamma tocopherol homologues and a delta tocopherol homologue fraction.

5. A process for isolating α-tocopheryl esters from other tocopheryl ester homologues (β-, γ-, δ-tocopheryl esters) according to claim 4 which comprises reacting the mixture of esters with pyrrolidine to deacylate the β-, γ-, and δ-tocopheryl esters, then separating the α-tocopheryl ester fraction from the tocopherol fraction.

6. A process for isolating beta-gamma tocopherols from a mixture of tocopherol ester homologues according to claim 4 which comprises: (1) reacting the mixture of esters with pyrrolidine to deacylate predominantly the δ-tocopheryl esters, (2) isolation of the remaining tocopheryl esters, (3) reacting the remaining isolated tocopheryl esters with pyrrolidine to provide a mixture of free beta-gamma tocopherols and α-tocopherol ester, and (4) separation of the tocopherol components from the α-tocopheryl ester.

* * * * *